United States Patent [19]

Gattuso

[11] 4,003,718
[45] Jan. 18, 1977

[54] SUBSTITUTED TETRAHYDROPYRIMIDINES

[75] Inventor: Marion J. Gattuso, Hoffman Estates, Ill.

[73] Assignee: Universal Oil Products Company, Des Plaines, Ill.

[22] Filed: Mar. 12, 1975

[21] Appl. No.: 557,744

[52] U.S. Cl. .............. 44/63; 44/DIG. 1; 252/390; 252/392; 260/256.4 H; 260/247.5 D
[51] Int. Cl.² ......................... C10L 1/14
[58] Field of Search ......... 260/256.4 H, 247.5 D; 44/63, DIG. 1; 252/390, 392

[56] References Cited

UNITED STATES PATENTS

| 3,787,416 | 1/1974 | Cyba | 44/63 |
| 3,844,957 | 10/1974 | Robinson et al. | 44/63 |

*Primary Examiner*—Donald G. Daus
*Assistant Examiner*—James H. Turnipseed
*Attorney, Agent, or Firm*—James R. Hoatson, Jr.; Raymond H. Nelson; William H. Page, II

[57] ABSTRACT

Substituted tetrahydropyrimidines, both mono- and disubstituted, as exemplified by 2(2-N,N-dioctylamino-2-propyl)-3-tetradecyl-1,4,5,6-tetrahydropyrimidine, are useful as additives in petroleum distillates such as gasoline.

13 Claims, No Drawings

SUBSTITUTED TETRAHYDROPYRIMIDINES

This invention relates to novel compounds comprising substituted tetrahydropyrimidines. More specifically, the invention relates to both mono- and disubstituted tetrahydropyrimidines which are useful as additives to petroleum distillates.

The novel compounds of the present invention which, as hereinbefore set forth, comprise tetrahydropyrimidines, are useful as additives which, when added to petroleum distillates, will provide certain beneficial effects thereto. For example, when these compounds are added to petroleum distillates such as gasoline, they will maintain the cleanliness of engine parts, protect against icing and stalling, as well as providing anti-rust protection by acting as a corrosion inhibitor. Likewise, when added to fuel oils, the additives will act as stabilizers or dispersants as well as imparting a detergent action by their presence. By acting as corrosion inhibitors, the additives, when added to petroleum distillates such as gasoline or fuel oil, will protect the distillate during storage and, in addition, the equipment which is necessary for handling such petroleum distillates during the production, storage and use thereof. In addition to the aforementioned uses, it is also contemplated that the novel compounds of the present invention may be used as chelating agents.

It is therefore an object of this invention to provide novel compositions of matter which are useful as additives for petroleum distillates.

A further object of this invention is to provide novel compounds which are useful as additives for petroleum distillates, said compounds being prepared in a two-step process hereinafter set forth in greater detail.

In one aspect an embodiment of this invention resides in a substituted tetrahydropyrimidine having the generic formula:

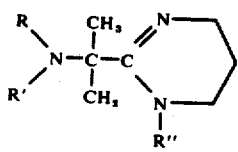

in which R and R' are independently selected from the group consisting of alkyl, cycloalkyl and aryl radicals or taken together form a heterocyclic ring and R" is hydrogen or an alkyl radical.

Another embodiment of this invention resides in a petroleum distillate containing, as an additive therefor, an effective amount of a substituted tetrahydropyrimidine having the generic formula:

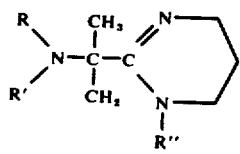

in which R and R' are independently selected from the group consisting of alkyl, cycloalkyl and aryl radicals or taken together form a heterocyclic ring and R" is hydrogen or an alkyl radical.

A specific embodiment of this invention resides in a novel compound comprising 2(2-N,N-dioctylamino-2-propyl)-3-tetradecyl-1,4,5,6-tetrahydropyrimidine.

Another specific embodiment of this invention is found in a gasoline containing, as an additive therefor, an effective amount of 2(2-morpholino-2-propyl)-3-tetradecyl-1,4,5,6-tetrahydropyrimidine.

Other objects and embodiments will be found in the following further detailed description of the present invention.

As hereinbefore set forth, the present invention is concerned with novel compounds comprising mono- and disubstituted tetrahydropyrimidines, said compounds being useful as additives for petroleum distillates. The novel compounds are prepared in a two-step process, the first step involving the reaction of acetone cyanohydrin with a disubstituted amine to form N,N-disubstituted-2-aminoisobutyronitrile. Thereafter this compound is then reacted with a 1,3-diaminopropane in a manner hereinafter set forth in greater detail.

The first step of the process, the reaction of an amine with acetone cyanohydrin, is effected at temperatures which may range from ambient (20°–25° C.) up to about 100° C. or more and preferably at a slightly elevated temperature which may range from about 30° to about 50° C. or more. In addition, another parameter of the reaction will involve the use of pressure, said pressure ranging from subatmospheric up to about 100 atmospheres, the operating variables of temperature and pressure being dependent upon the particular amine which is undergoing reaction with the acetone cyanohydrin. For example, if it is desired to remove the water which is formed during the reaction, it is possible to use reduced pressure without utilizing an azeotroping agent in the reaction medium. Examples of amines which may be reacted with the acetone cyanohydrin will comprise those amines possessing the generic formula:

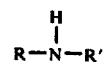

in which R and R' are independently selected from the group consisting of alkyl of from 1 to about 20 carbon atoms, cycloalkyl of from 3 to about 8 carbon atoms in the ring and aryl radicals or R and R' may be taken together to form a heterocyclic ring. Some representative examples of these amine compounds will include dimethyl amine, diethyl amine, dipropyl amine, dibutyl amine, di-t-butyl amine, the isomeric dipentyl amine, dihexyl amine, diheptyl amine, dioctyl amine, dinonyl amine, didecyl amine, diundecyl amine, didodecyl amine, ditridecyl amine, ditetradecyl amine, dipentadecyl amine, dihexadecyl amine, diheptadecyl amine, dioctadecyl amine, dinonadecyl amine, dieicosyl amine, dicyclopropyl amine, dicyclobutyl amine, dicyclopentyl amine, dicyclohexyl amine, dicycloheptyl amine, dicyclooctyl amine, diphenyl amine, di-o-tolyl amine, di-m-tolyl amine, di-p-tolyl amine, dibenzyl amine, pyrrole, morpholine, 1,4-oxazine, etc. It is to be understood that it is also contemplated within the scope of this invention that the R and R' substituents hereinbefore characterized may be different in nature thus forming an unsymmetrical amine which is reacted with the acetone cyanohydrin. Some representative examples of these compounds will include methyl ethyl amine, methyl propyl amine, methyl butyl amine, methyl pentyl amine, methyl hexyl amine, methyl octyl amine, methyl decyl amine, methyl tetradecyl amine, ethyl hexyl amine, ethyl heptyl amine, ethyl octyl amine, ethyl decyl amine, ethyl dodecyl amine, ethyl tetradecyl amine, propyl decyl amine, propyl tetradecyl amine, propyl hexadecyl amine, methyl cyclohexyl amine, methyl cycloheptyl amine, ethyl cyclohexyl amine, ethyl cycloheptyl amine, propyl cyclopentyl amine, propyl cyclohexyl amine, propyl cycloheptyl amine, methyl phenyl amine, methyl p-tolyl amine, methyl benzyl amine, ethyl phenyl amine, ethyl p-tolyl amine, ethyl benzyl amine, propyl phenyl amine, propyl p-tolyl amine, propyl benzyl amine, cyclohexyl phenyl amine, cyclohexyl benzyl amine, etc. It is to be understood that the aforementioned amines are only representative of the class of compounds which may be reacted with the acetone cyanohydrin and that the present invention is not necessarily limited thereto.

The compounds which result from the aforementioned reaction between the amine and the acetone cyanohydrin will comprise substituted 2-aminoisobutyronitriles possessing the generic formula:

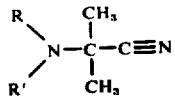

in which R and R' substituents are selected from the class of compounds hereinbefore set forth. Some specific examples of these compounds will include N,N-dimethyl 2-aminoisobutyronitrile, N,N-diethyl 2-aminoisobutyronitrile, N,N-dipropyl 2-aminoisobutyronitrile, N,N-dibutyl 2-aminoisobutyronitrile, N,N-dioctyl 2-aminoisobutyronitrile, N,N-dinonyl 2-aminoisobutyronitrile, N,N-didecyl 2-aminoisobutyronitrile, N,N-ditridecyl 2-aminoisobutyronitrile, N,N-ditetradecyl 2-aminoisobutyronitrile, N,N-dihexadecyl 2-aminoisobutyronitrile, N,N-diheptadecyl 2-aminoisobutyronitrile, N,N-dieicosyl 2-aminoisobutyronitrile, N,N-dicyclopentyl 2-aminoisobutyronitrile, N,N-dicyclohexyl 2-aminoisobutyronitrile, N,N-diphenyl 2-aminoisobutyronitrile, N,N-dibenzyl 2-aminoisobutyronitrile, N,N-di-p-tolyl 2-aminoisobutyronitrile, 2-morpholinoisobutyronitrile, etc. These compounds are then reacted with a diaminopropane to form the desired product.

The 1,3-diaminopropanes which are utilized as one of the reactants in the process of this invention will possess the generic formula:

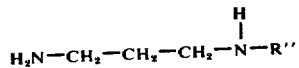

in which R" comprises hydrogen or an alkyl radical containing from 1 to about 20 carbon atoms or more in length. Some specific examples of these diaminopropanes which may be used will include 1,3-diaminopropane, N-methyl-1,3-diaminopropane, N-ethyl-1,3-diaminopropane, N-propyl-1,3-diaminopropane, N-butyl-1,3-diaminopropanes, N-pentyl-1,3-diaminopropane, N-hexyl-1,3-diaminopropane, N-heptyl-1,3-diaminopropane, N-octyl-1,3-diaminopropane, N-nonyl-1,3-diaminopropane, N-decyl-1,3-diaminopropane, N-undecyl-1,3-diaminopropane, N-dodecyl-1,3-diaminopropane, N-tridecyl-1,3-diamino-propane, N-tetradecyl-1,3-diaminopropane, N-pentadecyl-1,3-diaminopropane, N-hexadecyl-1,3-diaminopropane, N-heptadecyl-1,3-diaminopropane, N-octadecyl-1,3-diaminopropane, N-nonadecyl-1,3-diaminopropane, N-eicosyl-1,3-diaminopropane, etc. It is to be understood that the aformentioned substituted 1,3-diaminopropanes are only representative of the class of compounds and that the present invention is not necessarily limited thereto.

The reaction between the substituted 2-aminoisobutyronitriles and the 1,3-diaminopropanes is effected under reaction conditions which will include a temperature in the range of from about 50° up to about 150° C. and preferably at atmospheric pressure, although it is also contemplated within the scope of this invention that superatmospheric pressures ranging from 2 to about 100 atmospheres or more may be employed, the particular reaction conditions of temperature and pressure being dependent upon the reactants which are undergoing condensation as well as the desired reaction time, the latter being in a range of from about 0.5 up to about 20 hours or more in duration. In addition, the reaction is effected in the presence of a catalyst, the preferred catalyst for this reaction comprises elemental sulfur, although it is also contemplated that other sulfur-containing compounds may also be employed, although not necessarily with equivalent results. Some specific example of the novel compounds of the present invention which possess the generic formula:

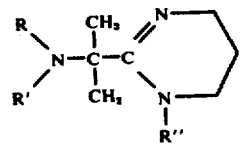

in which R and R' are independently selected from the group consisting of alkyl of from 1 to about 20 carbon atoms, cycloalkyl of from 5 to about 8 carbon atoms and aryl radicals or taken together form a heterocyclic ring and R" is hydrogen or an alkyl radical will include 2(2-N,N-dimethylamino-2-propyl)-1,4,5,6-tetrahydropyrimidine, 2(2-N,N-diethylamino-2-propyl)-1,4,5,6-tetrahydropyrimidine, 2(2-N,N-dipropylamino-2-propyl)-1,4,5,6-tetrahydropyrimidine, 2(2-N,N-dibutylamino-2-propyl)-1,4,5,6-tetrahydropyrimidine, 2(2-N,N-dioctylamino-2-propyl)-1,4,5,6-tetrahydropyrimidine, 2(2-N,N-dinonylamino-2-propyl)-1,4,5,6-tetrahydropyrimidine, 2(2-N,N-didecylamino-2-propyl)-1,4,5,6-tetrahydropyrimidine, 2(2-N,N-didodecylamino-2-propyl)-1,4,5,6-tetrahydropyrimidine, 2(2-N,N-ditetradecylamino-2-propyl)-1,4,5,6-tetrahydropyrimidine, 2(2-N,N-diphenylamino-2-propyl)-1,4,5,6-tetrahydropyrimidine, 2(2-N,N-dibenzylamino-2-propyl)-1,4,5,6-tetrahydropyrimidine, 2(2-N,N-di-p-tolylamino-2-propyl)-1,4,5,6-tetrahydropyrimidine, 2(2-N,N-dicyclopentylamino-2-propyl)-1,4,5,6-tetrahydropyrimidine, 2(2-N,N-dicyclohexylamino-2-propyl)-1,4,5,6-tetrahydropyrimidine, 2(2-N,N-dicycloheptylamino-2-propyl)-1,4,5,6-tetrahydropyrimidine, 2(2-N-methyl-N-propylamino-2-propyl)-1,4,5,6-tetrahydropyrimidine, 2(2-N-ethyl-N-propylamino-2-propyl)-1,4,5,6-tetrahydropyrimidine, 2(2-N-propyl-N-octylamino-2-propyl)- 1,4,5,6-tetrahydropyrimidine, 2(2-N-butyl-N-decylamino-2-propyl)-1,4,5,6-tetrahydropyrimidine, 2(2-N-pentyl-N-tetradecylamino-2-propyl)-1,4,5,6-tetrahydropyrimidine, 2(2-N-octyl-N-cyclohexylamino-2-propyl)-1,4,5,6-tetrahydropyrimidine, 2(2-N-octyl-N-phenylamino-2-propyl)-1,4,5,6-tetrahydropyrimidine, 2(2-N,N-dimethylamino-2-propyl)-3-octyl-1,4,5,6-tetrahydropyrimidine, 2(2-N,N-dioctylamino-2-propyl)-3-octyl-1,4,5,6-tetrahydropyrimidine, 2(2-N,N-didecylamino-2-propyl)-3-octyl-1,4,5,6-tetrahydropyrimidine, 2(2-N,N-ditetradecylamino-2-propyl)-3-octyl-1,4,5,6-tetrahydropyrimidine, 2(2-N,N-dicyclohexylamino-2-propyl)-3-octyl-1,4,5,6-tetrahydropyrimidine, 2(2-N,N-dicyclopentylamino-2-propyl)-3-octyl-1,4,5,6-tetrahydropyrimidine, 2(2-N,N-diphenylamino-2-propyl)-3-octyl-1,4,5,6-tetrahydropyrimidine, 2(2-N,N-dibenzylamino-2-propyl)-3-octyl-1,4,5,6-tetrahydropyrimidine, 2(2-N,N-dimethylamino-2-propyl)-3-decyl-1,4,5,6-tetrahydropyrimidine, 2(2-N,N-dioctylamino-2-propyl)-3-decyl-1,4,5,6-tetrahydropyrimidine, 2(2-N,N-didecylamino-2-propyl)-3-decyl-1,4,5,6-tetrahydropyrimidine, 2(2-N,N-ditetradecylamino-2-propyl)-3-decyl-1,4,5,6-tetrahydropyrimidine, 2(2-N,N-dicyclohexylamino-2-propyl)-3-decyl-1,4,5,6-tetrahydropyrimidine, 2(2-N,N-dicyclopentylamino-2-propyl)-3-decyl-1,4,5,6-tetrahydropyromidine, 2(2-N,N-diphenylamino-2-propyl)-3-decyl-1,4,5,6-tetrahydropyrimidine, 2(2-N,N-dibenzylamino-2-propyl)-3-decyl-1,4,5,6-tetrahydropyrimidine, 2(2-N,N-dimethylamino-2-propyl)-3-tetradecyl-1,4,5,6-tetrahydropyrimidine, 2(2-N,N-dioctylamino-2-propyl)-3-tetradecyl-1,4,5,6 -tetrahydropyrimidine, 2(2-N,N-didecylamino-2-propyl)-3-tetradecyl 1,4,5,6-tetrahydropyrimidine, 2(2-N,N-ditetradecylamino-2-propyl)-3-tetradecyl 1,4,5,6-tetrahydropyrimidine, 2(2-N,N-dicyclohexylamino-2-propyl)-3-tetradecyl-1,4,5,6-tetrahydroopyrimidine, 2(2-N,N-dicyclopentylamino-2-propyl)-3-tetradecyl-1,4,5,6-tetrahydropyrimidine, 2(2-N,N-diphenylamino-2-propyl)-3-tetradecyl-1,4,5,6-tetrahydropyrimidine, 2(2-N,N-dibenzylamino-2-propyl)-3-tetradecyl-1,4,5,6-tetrahydropyrimidine, 2(2-morpholino-2-propyl)-3-tetradecyl-1,4,5,6-tetrahydropyrimidine, etc. It is to be understood that, as in the case of the other lists of compounds, the aformentioned novel compounds of the present invention are only representative of the class of compounds which may be prepared and that said invention is not necessarily limited thereto.

The novel compounds of the present invention may be prepared in any suitable manner, said processes which are utilized being either a batch or continuous type of operation. For example, when a batch type operation is used, a quantity of the substituted amine of the type hereinbefore set forth in greater detail and the acetone cyanohydrin are reacted by placing the amine in an appropriate apparatus and slowly adding thereto the acetone cyanohydrin. The apparatus which is utilized may comprise a flask which is provided with cooling and heating means, the former being utilized to maintain a predetermined temperature range inasmuch as the addition of the acetone cyanohydrin to the amine will result in an exothermic reaction. It is contemplated within the scope of this invention that the reaction may be effected at elevated temperatures, in which case the heating means will be used to heat the flask and contents thereof to the desired temperature and maintain the temperature in a predetermined range during the residence time. It is also contemplated within the scope of this invention that the reaction may be effected in the presence of a substantially inert organic solvent including paraffins such as n-pentane, n-hexane, n-heptane, etc., cycloparaffins such as cyclopentane, cyclohexane, methylcyclopentane, etc., or aromatic solvents such as benzene, toluene, the xylenes, etc. One particular mode of operation which may be used when utilizing the inert organic solvent is to effect the reaction at the reflux temperature of the solvent utilizing a Dean-Stark trap to remove the water of reaction which is formed. At the end of the predetermined residence time, the apparatus is allowed to return to room temperature and the reaction mixture is recovered therefrom. This reaction mixture is then subjected to conventional means of separation and purification such as extraction, washing, drying, distillation, etc., whereby the substituted aminoisobutyronitrile is separated from any unreacted starting materials and solvent, if one is used, and recovered.

Following the preparation of the substituted aminoisobutyronitrile, this compound is then reacted with a 1,3-diaminopropane of the type hereinbefore set forth in greater detail at elevated temperatures ranging, as hereinbefore set forth, from about 50° up to about 150° C. or more. Due to the utilization of a 1,3-diaminopropane as the reactant with the aminoisobutyronitrile, the reaction product will comprise the condensation product resulting from the reaction between these two reactants and will not be a polymerization product. The reaction is effected by placing the two reactants in substantially equimolar proportions in an appropriate apparatus along with the catalyst which, in the preferred embodiment of the invention, comprises elemental sulfur. The apparatus and contents thereof are heated to the predetermined reaction temperature and maintained thereat for the desired residence time which may range from about 0.5 up to about 20 hours or more in duration. Upon completion of the desired residence time, heating is discontinued and the apparatus and contents thereof are allowed to return to room temperature. The reaction mixture is recovered and again subjected to conventional means of separation similar in nature to those hereinbefore set forth whereby the desired product comprising a substituted tetrahydropyrimidine is separated and recovered.

It is also contemplated within the scope of this invention that the novel compounds may be prepared in a continuous manner of operation. When such a type of operation is used, the reactants which are necessary to form the aminoisobutyronitrile, namely, the substituted amine and the acetone cyanohydrin, are continuously charged to a reaction zone which is maintained at the proper operating conditions of temperature and pressure. In addition, if so desired, an inert organic solvent of the type hereinbefore set forth may also be continuously charged to the reactor through a separate line or it may be admixed with one or both of the reactants and the resulting mixture charged thereto in a single stream. Upon completion of the desired residence time in the reactor, the reactor effluent is continuously withdrawn and subjected to fractional distillation whereby the desired aminoisobutyronitrile is separated from any unreacted starting materials and solvent, said unreacted starting materials and solvent being recycled to the reaction zone to form a portion of the feed stock while the aminoisobutyronitrile is continuously charged to a second reactor which is maintained at the proper operating conditions of temperature and pressure. The second reactor will contain the sulfur catalyst, preferably in solid form. In addition, the second reactant, namely, the substituted 1,3-diaminopropane, is continuously charged to the second reactor through a separate line or, if so desired, it may be admixed with the aminoisobutyronitrile prior to entry into said reactor and the resulting mixture charged thereto in a single stream. Inasmuch as the catalyst is in solid form, the condensation reaction in the second reactor may be effected in a variety of types of operation. One type of operation which may be employed comprises the fixed bed type of operation in which the reactants are passed over the catalyst bed in either an upward or downward flow. A second type of continuous operation which may be employed comprises the moving bed type of operation in which the reactants and the catalyst bed are passed through the reactor either concurrently or countercurrently to each other. As an alternate method of effecting the condensation reaction, the sulfur catalyst may be admixed with one or both of the reactants prior to entry into the reaction zone and the resulting mixture is passed as a slurry into said zone. As in the case of the first reactor, the reactor effluent is continuously withdrawn from this second reactor and subjected to conventional means of separation whereby the desired product comprising the substituted tetrahydropyrimidine is separated from any unreacted starting materials and catalyst, these unreacted starting materials and catalyst being recycled to the second reaction zone to form a portion of the feed stock.

The following examples are given as illustrations of the novel compounds of the present invention and to the use thereof as additives for petroleum distillates. However, it is to be understood that these examples are given merely for purposes of illustration and that the present invention is not necessarily limited thereto.

EXAMPLE I

In this example 200 cc. of benzene containing 241 grams (1.0 mole) of N,N-dioctyl amine is placed in an apparatus provided with a Dean Stark water trap. To this solution is slowly added 42.5 grams (0.5 mole) of acetone cyanohydrin, the addition taking place during a period of 30 minutes. The solution is refluxed for a period of 4 hours during which time the water of reaction which is formed is removed and collected. At the end of the 4-hour period, heating is discontinued and the mixture is subjected to fractional distillation, the desired N,N-dioctyl 2-aminoisobutyronitrile being recovered therefrom.

Following this, one molecular proportion of the aforementioned N,N-dioctyl 2-aminoisobutyronitrile is placed in a second flask along with one molecular proportion of N-tetradecyl-1,3-diaminopropane and a catalytic amount of elemental sulfur. The flask is heated to a temperature of 100° C. and maintained thereat for a period of 4 hours. At the end of this time, heating is discontinued and the reaction mixture is recovered therefrom. The liquid portion of the reaction is separated from the elemental sulfur by filtration, washed, extracted with benzene and subjected to fractional distillation whereby the novel compound of the present invention, namely 2(2-N,N-dioctylamino-2-propyl)-3-tetradecyl-1,4,5,6-tetrahydropyrimidine is separated and recovered.

EXAMPLE II

In a manner similar to that hereinbefore set forth, 181 grams (1.0 mole) of N,N-dicyclohexyl amine and 85 grams (1.0 mole) of acetone cyanohydrin are reacted, said reaction being effected in a benzene medium in a flask provided with a Dean Stark water trap. The reaction is effected at reflux temperature for a period of 2 hours during which time the water of reaction which forms is removed and collected. At the end of the 2-hour period, the reaction mixture is subjected to distillation under reduced pressure to remove the benzene solvent and the desired product comprising N,N-dicyclohexyl 2-aminoisobutyronitrile is recovered.

The desired compound is then prepared by reacting equimolecular proportions of the N,N-dicyclohexyl 2-aminoisobutyronitrile and N-tetradecyl-1,3-diaminopropane in the presence of elemental sulfur and a benzene solvent at a temperature of 100° C. for a period of 4 hours, said reaction being effected at atmospheric pressure in a reaction flask. At the end of the aforementioned residence time, the reaction mixture is separated from the elemental sulfur, washed, extracted, dried and subjected to fractional distillation, whereby the resulting 2(2-N,N-dicyclohexylamino-2-propyl)-3-tetradecyl-1,4,5,6-tetrahydropyrimidine is recovered.

EXAMPLE III

In this example 85 grams (1.0 mole) of acetone cyanohydrin is slowly added dropwise with stirring to a solution of 87 grams (1.0 mole) of morpholine in 200 cc of benzene. The temperature of the reaction, which is exothermic in nature, is maintained in a range of from about 25° to 35° C. by means of an ice bath during the addition of the acetone cyanohydrin. Upon completion of the addition of the acetone cyanohydrin, the mixture is heated to reflux and maintained thereat for a period of 4 hours, the water of reaction which is formed being removed and collected in a Dean Stark water trap. Upon completion of the reaction, the benzene solvent is removed in vacuo and the resultant N,N-oxydiethylene 2-aminoisobutyronitrile is recovered. The product which is thus prepared is then reacted with an equimolar amount of N-tetradecyl-1,3-diaminopropane in the presence of a catalytic amount of elemental sulfur, said reaction being effected at a temperature of 100° C. for a period of 4 hours. At the end of the 4-hour period, the reaction mixture is recovered and separated from the elemental sulfur, washed, dried and extracted with benzene, following which the mixture is subjected to fractional distillation whereby the desired product comprising 2(2-morpholino-2-propyl)-3-tetradecyl-1,4,5,6-tetrahydropyrimidine is recovered.

EXAMPLE IV

To a stirred solution of 200 cc of benzene containing 169 grams (1.0 mole) of N,N-diphenyl amine is slowly added dropwise 42.5 grams (0.5 mole) of acetone cyanohydrin. The temperature of the reaction is maintained in a range of from 25° to 35° C. by means of an ice bath due to the exothermic nature of the reaction. At the end of the addition period, the mixture is heated to reflux and maintained thereat for a period of 2 hours, during which time the water of reaction is removed and collected by means of a Dean Stark water trap. At the end of the 2-hour period, the benzene solvent and the excess N,N-diphenyl amine is removed by vacuum distillation, the resulting N,N-diphenyl 2- aminoisobutyronitrile being recovered. This product is then condensed with an equimolar amount of N-octyl-1,3-diaminopropane in the presence of a catalytic amount of elemental sulfur, said reaction being effected at atmospheric pressure and a temperature of 100° C. for a period of 4 hours in a reaction flask. At the end of the 4-hour period, heating is discontinued, and the reaction mixture is separated from the elemental sulfur by filtration. The liquid product is washed, dried, extracted with benzene and the benzene extract is subjected to distillation whereby the desired product comprising 2(2-N,N-diphenylamino-2-propyl)-3-octyl-1,4,5,6-tetrahydropyrimidine is separated and recovered.

EXAMPLE V

A reaction flask is provided with cooling means and a Dean Stark water trap, said flask containing a solution of 129 grams (1.0 mole) of N,N-dibutyl amine in 200 cc of benzene. The reaction apparatus is maintained at a temperature of from 25° to 30° C. by means of an ice bath while 42.5 grams (0.5 mole) of acetone cyanohydrin is slowly added to the solution during a period of 30 minutes. The maintenance of the temperature of the solution in this range is necessary due to the exothermic nature of the reaction between the acetone cyanohydrin and the N,N-dibutyl amine. Upon completion of the addition of the acetone cyanohydrin, the mixture is then heated to reflux and maintained thereat for a period of 2 hours, during which time the water of reaction which forms is removed and collected. Upon completion of the 2-hour period, the benzene solvent and the excess N,N-dibutyl amine are removed by distillation and the resulting N,N-dibutyl 2-aminoisobutyronitrile is recovered. The desired product of the present invention is prepared by reacting an equimolecular proportion of the thus prepared N,N-dibutyl 2-aminoisobutyronitrile with 1,3-diaminopropane, the reaction being effected in a benzene solvent and in the presence of a catalyst comprising elemental sulfur at a temperature of 100° C. for a period of 4 hours. At the end of the 4-hour period, heating is discontinued and the reaction mixture is recovered. After separation from the elemental sulfur the mixture is washed, dried and subjected to distillation whereby the desired product comprising 2(2-N,N-dibutylamino-2-propyl)-1,4,5,6-tetrahydropyrimidine is recovered.

EXAMPLE VI

As an illustration of the ability of the additive formulation of the present invention to impart desirable characteristics to petroleum distillates, a carburetor icing test was performed in which both regular and premium type gasoline were evaluated with and without the additive formulation of the present invention.

The anti-icing properties were determined in a carburetor icing demonstration apparatus consisting of a vacuum pump equipped so that cool moisture-saturated air from an ice tower is drawn through a simulated carburetor. The gasoline sample passes from a fuel reservoir through a flow meter into the carburetor at a rate of 1.4 lb/hr. The air from the ice tower is passed at a flow rate of 14.4 lb/hr at a temperature of 40° F. In addition, the manifold vacuum is 9.5" of mercury at the start and 12.5 at the end of the test. Evaporation of the gasoline in the carburetor further cools the cold moist air, with resulting ice formation on the throttle plate. The time in seconds is measured until a drop of 3" of mercury vacuum occurs which indicates stalling conditions. The regular type gasoline which was used in this experiment reached stalling conditions within about 16.5 seconds. In contrast to this, when an additive comprising 2(2-N,N-dicyclohexylamino-2-propyl)-3-tetradecyl-1,4,5,6-tetrahydropyrimidine is added to the gasoline in concentrations of 10, 30 and 50 ppm of gasoline, it will be found that the stalling times will be increased to a much longer length of time.

EXAMPLE VII

As an additional example of the ability of the additives of the present invention to afford desirable characteristics to petroleum distillates, a carburetor detergency test is performed. The additive formulation in concentrations of 50 ppm is used in connection with both regular base and premium base gasolines. The blank fuels, that is, both regular base and premium base gasolines, which contain no additives, will afford very dirty carburetor throat bodies after a standard 5 hour test cycle. In contradistinction to this, when 2(2-morpholino-2-propyl)-3-tetradecyl-1,4,5,6-tetrahydropyrimidine is added to both regular base and premium base gasoline, it will be found that the additive will be effective in keeping carburetor deposits to a relatively low level on the throttle plate of a carburetor.

EXAMPLE VIII

As a further illustration of the usefulness of the novel compounds of the present invention as additives for petroleum distillates, a water emulsibility test method as developed by Union Oil Company can be used. The test method which is used comprises adding approximately 600 cc of gasoline to a mixing vessel, following which exactly 6 cc of distilled water is then pipetted into the gasoline. The water and gasoline are then stirred for a period of exactly 10 minutes utilizing a stopwatch which is started with water addition. At the end of the 10-minute period, the stopwatch is quickly set to zero and started so that all subsequent times are measured from the moment that stirring is stopped.

A siphon tube is then placed into the liquid and clamped into such a position which has been preset to siphon the correct volume. At exactly 30 seconds from the time that stirring is stopped, the siphon is started using a suction bulb and 450 cc of the gasoline-water mixture is transferred to a settling vessel. The settling vessel is provided at the lower end thereof with a 15 cc calibrated centrifuge tube. The siphon tube is then removed and a loose stopper is placed on the settling vessel. The volume of water which has dropped to the bottom of the settling vessel is recorded at intervals of 1.5 minutes, 2 minutes and at each minute thereafter through 10 minutes. Following this, the volume of water is further recorded at intervals of 15, 20, 30, 60, 90 and 120 minutes. After the fuel has reached the clear point, any water drops which remain on the walls of the settling tube are loosened by use of a rubber policeman and a final water volume is read.

Additional quantitative data which may be taken include a time for the gasoline to reach a light haze point and a clear point. Also the percents by volume of water phase that is emulsion is recorded at each water volume reading through the 2-hour period. The light haze point is defined as the time when two parallel red lines on a white card which are observed horizontally through the gasoline can first be resolved as two separate lines. The two lines are from 0.3 to 0.5 mm thick and are separated by a distance of 0.3 to 0.5 mm. The card containing these lines is held at the bottom of the main point of the settling vessel just above the shoulder of the vessel. The clear point is the time at which the gasoline first reaches a bright and clear condition. This point is best judged by looking vertically down into the vessel. Observation of both the light haze and the clear point are made each 15 minutes following 30 minutes and beyond 120 minutes as necessary to catch the points.

The water emulsibility rating is calculated from the following equation:

Emulsibility Rating = $D_1 + D_2 - T_1 - T_2 - E + 400$ $D_1$ = Percent by volume of water which drops out in 30 seconds $D_2$ = Percent by volume of water which drops out in 10 minutes $T_1$ = Minutes for gasoline to reach the light haze point $T_2$ = Minutes for gasoline to clear E = Percent by volume of water layer in the settling vessel that is emulsion after 2 hours of settling The constant of 400 is added to give positive ratings for any additives.

Normally, the emulsion, if present, is a clearly recognized fraction of the water layer. If the water is cloudy, it is considered to be 20% emulsion; very cloudy water is considered to be 100% emulsion.

One test is run with gasoline which contains no additives while a second test is run with gasoline which contains 35 ppm of 2(2-N,N-dioctylamino-2-propyl)-3-tetradecyl-1,4,5,6-tetrahydropyrimidine. The comparative tests which are obtained from these two runs will show that the gasoline sample which contains the additive of the present invention will approach the values of the gasoline which contains no additives and that no emulsion will be found in the gasoline which contains the compound of the present invention.

EXAMPLE IX

In addition to the tests which were performed utilizing the compounds of the present invention in gasoline, another test is performed to illustrate the activity of the compounds to act as fuel oil stabilizers. The one-day fuel oil stability test which is used consists of filtering the fuel oil through coarse filter paper to remove any sediment or emulsion which may be present. Following this, 1 liter of the fuel oil is measured into a flask containing 4 mild cold-rolled steel strips 5 × ½ 1/16" in size which have been sand blasted and rinsed with a solvent. In one flask 10 ppm of an additive formulation of the type set forth in Example I above is added to the fuel oil and the two flasks are swirled to thoroughly admix the mixture. An oxygen line is then placed in the flask and the air space is purged with oxygen for a period of 5 minutes. Following this, a Teflon sleeve is placed on the stopper of the flask, the flask is stoppered and the stopper is secured with steel springs. The flasks are then placed in an oil bath for a period of 16 hours while maintaining the temperature of the bath at 212° F. At the end of the 16 hours, the flasks are removed from the bath and allowed to return to room temperature for a period of 1 hour. An AA Millicore filter disc is weighed in a Petri dish. The fuel oil is then filtered through the disc into a clean suction flask, using a soft vacuum at the start of the filtration to avoid any possible damage to the filter. Upon completion of the filtration, a portion of the filtered oil is removed for a color determination. The flask and iron strips are then rinsed three times with 100 cc portions of solvent, said solvent being also filtered through the filter. The filter is then rinsed with a small amount of additional solvent to insure that all of the oil is washed through the filter. Thereafter the filter is suction dried by an additional vacuum treatment.

The filter is then removed and placed in the same Petri dish in which it had previously been weighed. The filter is then baked in an oven for 1 hour at a temperature of 95° C., following which the dish is removed, cooled in a dessicator for a period of 16 hours and reweighed. The net gain in weight is calculated as milligrams of sediment per liter. The total sediment which is formed is taken as an important criterion of fuel oil stability due to the fact that it correlates roughly with field performance.

When comparing a fuel oil which contains no additive with a fuel oil which contains 10 ppm of 2(2-N,N-diphenylamino-2-propyl)-3-octyl-1,4,5,6-tetrahydropyrimidine, it will be found that the fuel oil which contains the additive will possess a similar ASTM color as does the blank fuel oil and, in addition, will retard the tendency of the oil to form sediment.

I claim as my invention:

1. A substituted tetrahydropyrimidine having the generic formula:

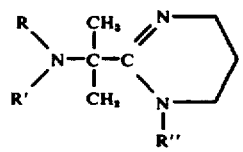

in which R and R' are independently selected from the group consisting of alkyl of from 1 to 20 carbon atoms, cycloalkyl of from 3 to 8 carbon atoms in the ring, phenyl and benzyl, and R" is hydrogen or alkyl of from 1 to 20 carbon atoms.

2. The substituted tetrahydropyrimidine of claim 1 being 2(2-N,N-dioctylamino-2-propyl)-3-tetradecyl-1,4,5,6-tetrahydropyrimidine.

3. The substituted tetrahydropyrimidine of claim 1 being 2(2-N,N-dicyclohexylamino-2-propyl)-3-tetradecyl-1,4,5,6-tetrahydropyrimidine.

4. The substituted tetrahydropyrimidine of claim 1 being 2(2-morpholino-2-propyl)-3-tetradecyl-1,4,5,6-tetrahydropyrimidine.

5. The substituted tetrahydropyrimidine of claim 1 being 2(2-N,N-diphenylamino-2-propyl)-3-octyl-1,4,5,6-tetrahydropyrimidine.

6. The substituted tetrahydropyrimidine of claim 1 being 2(2-N,N-dibutylamino-2-propyl)-1,4,5,6-tetrahydropyrimidine.

7. Petroleum distillate of the class of gasoline and fuel oil containing, as an additive therefor, from 10 to 50 ppm. of a substituted tetrahydropyrimidine as set forth in claim 1.

8. The petroleum distillate as set forth in claim 7 being gasoline.

9. The petroleum distillate of claim 7 in which the additive therefor is 2(2-N,N-dioctylamino-2-propyl)-3-tetradecyl-1,4,5,6-tetrahydropyrimidine.

10. The petroleum distillate of claim 7 in which the additive therefor is 2(2-N,N-dicyclohexylamino-2-propyl)-3-tetradecyl-1,4,5,6-tetrahydropyrimidine.

11. The petroleum distillate of claim 7 in which the additive therefor is 2(2-morpholino-2-propyl)-3-tetradecyl-1,4,5,6-tetrahydropyrimidine.

12. The petroleum distillate of claim 7 in which the additive therefor is 2(2-N,N-diphenylamino-2-propyl)-3-octyl-1,4,5,6-tetrahydropyrimidine.

13. The petroleum distillate of claim 7 in which the additive therefor is 2(2-N,N-dibutylamino-2-propyl)-1,4,5,6-tetrahydropyrimidine.

* * * * *